(12) United States Patent
Koivunen et al.

(10) Patent No.: US 8,785,158 B2
(45) Date of Patent: Jul. 22, 2014

(54) METHOD FOR DISSOLVING CELLULOSE AND FOR PRODUCING CELLULOSE PARTICLES

(75) Inventors: Kimmo Koivunen, Espoo (FI); Petri Silenius, Lohja (FI); Janne Laine, Espoo (FI); Tapani Vuorinen, Espoo (FI)

(73) Assignee: Sappi Netherlands Services B.V., Maastricht (NL)

( * ) Notice: Subject to any disclaimer, the term of this patent is extended or adjusted under 35 U.S.C. 154(b) by 1432 days.

(21) Appl. No.: 11/922,878

(22) PCT Filed: Jun. 27, 2006

(86) PCT No.: PCT/FI2006/050286
§ 371 (c)(1),
(2), (4) Date: Feb. 14, 2008

(87) PCT Pub. No.: WO2007/003699
PCT Pub. Date: Jan. 11, 2007

(65) Prior Publication Data
US 2009/0014902 A1    Jan. 15, 2009

(30) Foreign Application Priority Data
Jul. 1, 2005  (FI) ........................... 20055381

(51) Int. Cl.
*C12P 19/14*    (2006.01)
(52) U.S. Cl.
CPC ..................... *C12P 19/14* (2013.01)
USPC ........................... 435/99; 435/205
(58) Field of Classification Search
CPC ....................................... C12P 19/14
USPC ...................................... 435/99, 209
See application file for complete search history.

(56) References Cited

U.S. PATENT DOCUMENTS

| 3,642,580 A | * | 2/1972 | Ghose .................. 435/105 |
| 6,080,277 A | | 6/2000 | Oberkofler et al. |
| 6,174,358 B1 | | 1/2001 | Oberkofler et al. |

FOREIGN PATENT DOCUMENTS

| FI | 107335 B | | 1/1998 |
| GB | 1458955 A | | 12/1976 |
| PL | 167519 B1 | * | 10/1992 |
| WO | WO-99/16960 A1 | | 4/1999 |
| WO | WO-01/96402 A1 | | 12/2001 |

OTHER PUBLICATIONS

STN abstract for PL 167519 (Struszczyk et al.) Sep. 30, 1995; abstract only downloaded from CAPLUS on Jan. 2, 2011.*
English translation of PL 167519 to Struszczyk et al. published Oct. 19, 1992.*

* cited by examiner

*Primary Examiner* — Susan Hanley
(74) *Attorney, Agent, or Firm* — Birch, Stewart, Kolasch & Birch, LLP

(57) ABSTRACT

The invention relates to a method for dissolving cellulose e.g. for the production of regenerated cellulose products such as films, fibers, particles and the like. In said method, the cellulose material is dissolved using an enzymatic treatment, followed by a base treatment. The invention is also directed to a method for producing cellulose particles wherein cellulose dissolved as described above is sprayed or mixed into a regenerating solution for precipitating cellulose particles. Moreover, the invention relates to the use of said cellulose particles produced with this method as a filler and/or coating pigment of paper and board. The invention is also directed to methods for producing and coating paper and board.

6 Claims, 3 Drawing Sheets

METHOD FOR DISSOLVING CELLULOSE AND FOR PRODUCING CELLULOSE PARTICLES

FIELD OF THE INVENTION

Figure 1:
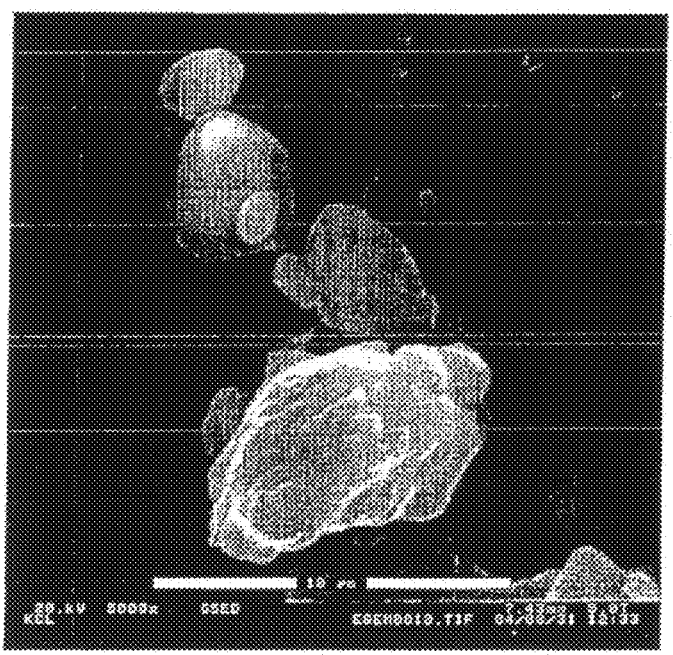

The present invention relates to a method for dissolving cellulose e.g. for the production of regenerated cellulose products. The invention is also directed to a method for producing cellulose particles. Moreover, the invention relates to the use of said cellulose particles produced with this method as a filler and/or coating pigment of paper and board. The invention is also directed to a method for producing and coating paper and board.

PRIOR ART

Various methods for producing solid cellulose products from dissolved cellulose are known. One of the most renowned methods is the viscose method wherein the cellulose material to be dissolved is contacted with NaOH yielding alkali cellulose. Thereafter, said alkali cellulose is treated with a compound containing sulphur by adding carbon disulphide thereto giving cellulose xanthate, or viscose, soluble in NaOH. Air and solid impurities are normally removed from the viscose by filtering. Regeneration is carried out by passing said viscose for instance through suitable nozzles to an acidic spinning bath, thus precipitating cellulose. The cellulose products thus obtained may be finally washed, dried and cut.

In another known process for producing cellulose products, cuprammonium is utilized for producing e.g. rayon. In this process, a cellulose starting material is dissolved in an aqueous solution of cuprammonium and converted to desired products by passing the solution to baths regenerating cellulose.

Cellulose may also be dissolved in a solvent containing lithium chloride, for instance in lithium chloride/N,N-dimethyl acetamide solution. In this case, regeneration of cellulose is performed for instance in alcohol or aqueous alcohol.

In still another known process, cellulose is dissolved in an organic solvent, typically in a tertiary N-oxide followed by the formation of the cellulose products from this solution and washing off the solvent. Among others, Lyocell fibres are produced by this method.

Complex processes with several steps are necessary in the methods described above, said processes being difficult to control, expensive and/or requiring chemicals very hazardous to humans and environment. In an effort to eliminate these problems, methods using enzyme treatments have been developed.

FI 107335 describes a method for producing cellulose soluble in an aqueous alkali metal hydroxide solution, and further, a method for producing fibres, films or other products from cellulose. Cellulose pulp is treated with a mixture of cellulase enzymes, followed by dissolution in an aqueous alkali metal hydroxide solution, particularly in an aqueous solution of sodium or potassium hydroxide having a concentration ranging between 5 and 15%, by weight, at a temperature varying from −10 to +10° C. Air is removed from the cellulose solution, followed by the optional filtering of said solution prior to formation of the cellulose products in regeneration baths.

Patent application WO 01/96402 describes a method for producing cellulose fibres, films and other cellulosic products. In this method, cellulose is suspended in water, in a buffer having a pH of at least 2.5 and/or in an aqueous enzyme solution, followed by mechanical and/or enzymatic pretreatment of said cellulose. After the removal of any excessive solution, an enzymatic treatment using an aqueous solution of enzymes of the cellulase type is performed, excess of the enzyme solution is removed, followed by the deactivation of the enzymes by washing with water having a temperature more than 60° C. The cellulose thus obtained is dissolved in an aqueous alkali metal hydroxide while vigorously agitating, at a temperature of at least 0° C., elevating the temperature to a value between 5 and 12° C. at the end of the dissolution. The cellulose solution is filtered, and air is eliminated prior to formation of the cellulose products in regenerating baths.

Drawbacks of known methods using enzymatic treatment include e.g. low solubility of the enzymatically treated cellulose and instability of the cellulose solution requiring very low temperatures during dissolution. Moreover, additional process steps are necessary to perform these complicated pretreatment procedures, separate elimination of the enzyme solution, and inactivation, said additional process steps further adding to the complexity of the process and costs, and reducing the ability to control the process.

On the basis of the above teachings it may be seen that there is a need for a simple and efficient, environmentally friendly method for dissolving cellulose to produce e.g. regenerated cellulose products such as films, fibres, particles and the like.

Light and organic cellulose particles may be produced by the method for dissolving cellulose of the invention. Such cellulose particles may be used as fillers and coating pigments in the production of paper and board.

Optical properties and bonding strength, often referred to as Scott Bond value, are some of the most crucial properties of printing papers. For boards and papers in general, and particularly for graphical papers, there is a need to improve the strength properties without any adverse effects on the optical properties.

Burning of waste papers containing inorganic mineral pigments for energy production results in great amounts of ash, the disposal of which causes problems. Within the European Union, aims concerning the proportion of bioenergy in the total energy production to be reached until 2010 are set. For these aims, it is also desirable to use in papers and boards as much renewable organic materials as possible.

Inorganic mineral pigments are abrasive and result in accelerated wear of apparatuses. They also increase the weight of paper and board. There is an ever growing need for increasingly lighter papers for magazines, catalogues and the like, furnished, however, with high quality printing properties.

As may be seen on the basis of the above teachings, there is a need for lighter fillers and coating pigments for papers and boards allowing for the improvement of the strength properties thereof without any detrimental effects on optical properties, and further allowing for the increase of the proportion of renewable and combustible organic materials therein, and the reduction of wear of the equipment.

OBJECTS OF THE INVENTION

An object of the invention is to provide a method for dissolving cellulose for instance to produce cellulose products such as films, fibres, particles and the like that may be regenerated.

Another object of the invention is to provide a method for producing cellulose particles.

Still an object of the invention is the use of cellulose particles as fillers in papers and boards, and further, as a coating pigment for producing paper and board.

Still another object of the invention is to provide a method for producing paper and board.

Another object of the invention is to provide a method for coating paper and board.

Characteristic features of the inventive method for dissolving cellulose and for producing cellulose particles, use of said cellulose particles, as well as coating and production methods for paper and board are presented in the claims.

SUMMARY OF THE INVENTION

The invention is directed to a method for dissolving cellulose for instance to produce regenerated cellulose products such as films, fibres, particles and the like in a simple, efficient and environmentally friendly manner. In the method of the invention, optionally ground cellulose is dissolved by an enzymatic treatment, followed by a base treatment.

The invention also relates to a method for producing cellulose particles useful for the production and coating of paper and board. In the method of the invention for producing cellulose particles, cellulose is dissolved by the described method comprising said enzyme and base treatments, followed by spraying or mixing the cellulose solution obtained to a regenerating solution for the precipitation of cellulose particles.

Cellulose particles produced with the method of the invention may be used as fillers of paper and board for improving the strength properties of the product without any detrimental effects on optical properties. Cellulose particles produced by the method of the invention may further be used as coating pigments of paper and board.

The invention is now illustrated with the following figures, detailed description and examples without wishing to limit the invention thereto.

A BRIEF DESCRIPTION OF THE DRAWINGS

FIG. 1 shows an electron micrograph (magnification ×5000) of cellulose particles produced with the method of the invention according to Example 1.

FIGS. 2a-2d graphically show properties of sheets of Example 3 containing about 6% and 14% by weight of cellulose particles produced with the method of the invention and stiffened by the formaldehyde treatment of example 2 (Alk-Bead6 cross linked). FIGS. 2a, 2b, 2c and 2d respectively present the tensile index as a function of filler content, bonding strength as a function of filler content, light scattering coefficient as a function of the bonding strength, and the light scattering coefficient as a function of the tensile index. Sheets containing about 6, and 14% by weight of reference cellulose particles (ViscBead 4), microcrystalline cellulose (MCC1 and MCC2), and precipitated calcium carbonate (PCC), and moreover, a sheet without any filler serve as controls. Control cellulose particles are produced as the cellulose particles in Example 1, however, using cellulose dissolved by the viscose process.

DETAILED DESCRIPTION OF THE INVENTION

It was surprisingly found that problems encountered in the solutions of the prior art may be avoided or at least substantially reduced with the procedure of the invention. The invention is based on the finding that cellulose may be dissolved in a simple and efficient way by an enzymatic treatment and subsequent base treatment. The method of the invention for dissolving cellulose may be used for instance for the production of regenerated cellulose products such as films, fibres, particles and the like.

In the method of the invention, an aqueous suspension is prepared from the cellulose material to be dissolved, the cellulose content in said suspension being at least 0.1%, by weight. Prior to the preparation of the aqueous suspension, the cellulose material to be dissolved may be mechanically ground for increasing the efficiency of dissolution. Cellulose material to be dissolved may for instance be bleached softwood pulp, cellulosic waste from agriculture or forestry, or the like. The pH value of the suspension is adjusted to a range optimal for the activity of enzymes in the subsequent enzymatic treatment, said pH varying from 3 to 7, preferably from 4 to 6. The pH value may be adjusted with dilute NaOH and HCl solutions. Thereafter an enzyme is added to the suspension while optionally mixing, said enzyme meaning in this context enzyme mixtures with suitable enzymatic activities. Suitable enzymes mainly contain endoglucanase activity, that is cellulases. In case the enzyme mixture contains an excessive amount of exoglucanase activity, cellulose may be decomposed to give units that may no longer be regenerated due to too low molecular weights. As an exemplary enzyme useful in the method of the invention, the product Pergalase A40 may be mentioned, the optimum pH for the activity thereof being 5. The enzyme having endoglucanase activity is added in an amount resulting in an endoglucanase activity ranging between 20 and $2000*10^3$ IU/kg of dry pulp, preferably between 100 and $600*10^3$ IU/kg of dry pulp. The thus obtained suspension containing enzyme is heated at temperatures where the enzymes are active, said temperatures varying between about 40 and 65° C., preferably between 45 and 60° C., for 1 to 10 hours, or until the degree of polymerization of the cellulose is lowered not more than to a value of 100. Here, the degree of polymerization refers to the number of monomer units in the polymer. For the purpose of determining the degree of polymerization of cellulose, said cellulose is normally in solution. Mean degree of polymerization of cellulose may be assayed for instance by osmometry or by the determination of reducing end groups. After the enzymatic treatment, dissolution of cellulose is continued using the base treatment. To this end, alkali or alkaline earth metal hydroxide is added to the enzymatically treated suspension, optionally while mixing, in an amount more than 15% by weight, preferably from 15.5 to 30%, more preferably from 15.5 to 20%, by weight, followed by heating at temperatures ranging from 15 to 50° C., preferably from 20 to 45° C., for 1 to 10 hours or until at least 50% of said cellulose is dissolved. Dissolution may be determined by a method comprising filtering of the solution, and washing, drying and weighing of the precipitate. The alkali or alkaline earth metal hydroxide is preferably NaOH. Air may be eliminated after dissolving the cellulose. Also solids may be eliminated for instance by filtering.

Accordingly in the method of the invention for dissolving cellulose, an aqueous suspension is prepared from the cellulose material to be dissolved, the suspension having a cellulose content of at least 0.1% by weight; the pH value of the suspension is adjusted to a range from 3 to 7, preferably from 4 to 6; an enzyme with endoglucanase activity is added to the suspension in an amount resulting in endoglucanase activity from 20 to $2000 \times 10^3$ IU/kg of dry pulp, preferably from 100 to $600 \times 10^3$ IU/kg of dry pulp, and thereafter, the suspension containing the enzyme is heated at a temperature varying between 40 and 65° C., preferably between 45 and 60° C. until the degree of polymerization of the cellulose is lowered not more than to a value of 100; followed by the addition of an alkali or alkaline earth metal hydroxide in an amount above 15% by weight, and then heating at temperatures varying between 15 and 50° C., preferably between 20 and 45° C. until at least 50% of said cellulose is dissolved.

In the method of the invention for dissolving cellulose, said cellulose is dissolved as described above using treatments with an enzyme and a base, followed by passing the cellulose solution thus obtained into a regenerating solution to precipitate cellulose particles. The simplest way for the regeneration of the dissolved cellulose to give cellulose particles is by spraying or mixing the cellulose solution to the regenerating solution. In case regeneration is carried out by mixing, for instance by gradually adding the cellulose solution using a burette, the regenerating solution must be efficiently mixed, e.g. with a magnetic stirrer at 600 to 1000 rpm. In case the regeneration is carried out by spraying, a spray bottle equipped with a fan-like nozzle that may be adjusted in a stepless manner, or a like approach may be used. Spreading angle of the nozzle may for instance be selected from the range between 10° and 150°. Among other factors, suitable spreading angles depend on the distance between the nozzle and the regenerating solution. The greater the spraying distance, the smaller spreading angles may be used. In case spraying into the regenerating solution is carried out at a distance ranging from 20 to 30 cm, the suitable spreading angle varies between 20° and 60°. The regenerating solution is preferably acid, more preferably dilute sulphuric acid solution such as 1 M sulphuric acid solution. Further alternatives include other strong acids such as HCl, and moreover, $HClO_4$, HI, HBr and $HNO_3$ may be contemplated. The particles formed may be left in the regenerating solution for any post treatment such as coating, but the particles may also be recovered for washing and/or drying.

Thus in the method of the invention for producing cellulose particles, cellulose is dissolved as described above, followed by spraying or mixing the cellulose solution thus obtained into a regenerating solution to precipitate said cellulose particles.

In the production and coating of paper and board, particle size of the useful cellulose particles may typically vary between 0.05 and 10 µm. Particle size of the cellulose particles to be used as fillers preferably ranges from 1 to 2 µm. Particle size of the cellulose particles to be used as coating pigments preferably ranges from 0.2 to 1 µm. Particle sizes of the cellulose particles to be precipitated are adjusted to the desired range by selecting the parameters of the production process in a suitable manner, said parameters including the cellulose content and droplet size of the cellulose solution in case the cellulose solution is sprayed into the regenerating solution, or mixing speed in case the cellulose solution is mixed into the regenerating solution. The cellulose content of the cellulose solution may then be selected to be for instance between 0.05 and 1.5% by weight. Thus, according to an embodiment of the production method for cellulose particles of the present invention, the cellulose content of the cellulose solution, and the droplet size in case spraying is used, or mixing speed in case mixing is used are selected to produce precipitated particles having particle sizes between 0.05 and 10 µm.

According to the application of the cellulose particles produced using the method of the invention, it may be preferable for the cellulose particles to have some special properties. For instance, the stiffness of the structure of the cellulose particles may be advantageous for use e.g. in the production of paper and board. Said stiffness may be improved for instance by drying the cellulose particles. Thus, according to an embodiment of the present production method for cellulose particles, regenerated cellulose particles are washed and/or dried. Stiffness may also be improved by modifying the cellulose by the conversion thereof to give a derivative using any known methods following base treatment while said cellulose is dissolved, or only after regeneration to produce cellulose particles. Cellulose may for instance be acetylated using acetic anhydride. Thus, according to an embodiment of the present production method for cellulose particles, cellulose is converted to a derivative prior to precipitation thereof or following precipitation.

Stiffness is also improved by crosslinking the cellulose particles. According to still another embodiment, cellulose particles are provided with crosslinks by adding about 5 moles of formaldehyde per one mole of glucose units to the acidic suspension containing cellulose particles at room temperature, said suspension is heated at 40 to 60° C. and said cellulose particles are recovered. The formaldehyde to be used is e.g. formaldehyde having a concentration of 37% that may contain from 10 to 15% of methanol. Heating time may vary between 30 and 90 minutes. The acidity of the suspension containing cellulose particles is then about 0.1 M strong acid, for instance sulphuric acid.

Also the porosity of the cellulose particles may be advantageous for some applications. Porosity may be provided by adding any substance soluble under the regeneration conditions to the dissolved cellulose, for instance after the removal of air and solids. Since an acid is used for the regeneration, substances soluble under the regeneration conditions include e.g. starch and alkali and alkaline earth metal salts such as hydroxides. Most preferably magnesium hydroxide is added to the dissolved cellulose. In case cellulose particles are regenerated, these substances dissolve leaving holes and cavities in the structure of the particles, thus increasing the specific surface area. Accordingly, in still another embodiment of the method for producing cellulose particles, a substance soluble under the regeneration conditions, preferably starch or a an alkali or alkaline earth metal salt, more preferably magnesium hydroxide, is added to the dissolved cellulose.

The method of the invention for dissolving cellulose may be used to produce cellulose products for instance for paper, food, textile and pharmaceutical industries. The method of the invention may thus be used for producing cellulose particles suitable as fillers for paper and board, moreover for producing cellulose particles suitable as coating pigments for paper and board. It is also possible to use the method of the invention for the production of various tubular and flat films of regenerated cellulose for food packing application. Still another application of the inventive method may be the production of fibres for instance for textile industry. Examples of other possible applications of the method of the invention include the production of food additives such as various cellulose powders, and the production of particles and films for the pharmaceutical industry.

The method of the invention has several advantages in comparison to the prior art methods. The method is simple, low treatment temperatures may be avoided and no chemicals hazardous to humans or the environment are necessary. The degree of polymerization dissolved by this method is suitable for the use of this method in the production of regenerated cellulose products.

The cellulose particles produced by the method of the invention may be used as fillers in paper and board. The particle size of the cellulose particles to be used as fillers preferably ranges from 1 to 2 µm. The cellulose particles produced by the method of the invention are suitable as fillers both for fine papers and for papers containing mechanical pulp, examples including LWC, ULWC, MWC, and SC.

The cellulose particles produced by the method of the invention may also be used as a coating pigment for papers containing mechanical pulp such as for LWC printing papers, and further, as a coating pigment for boards, for instance FBB board. The particle size of the cellulose particles to be used as coating pigments preferably varies from 0.2 to 1 µm.

In the process of the invention for making paper or board, cellulose particles are added to the pulp during paper or board production at a suitable point of the system prior to the press section, preferably in the short circulation and particularly preferably at the proximity of the head box, such as at the suction side of the mixing pump, or at the proximity of the feed pump of the head box, in amounts resulting in filler contents in the paper or board, that is the amount of the cellulose particles varying between 1 and 50% by weight, followed by producing the paper or board in a conventional manner.

In the process of the invention for coating paper, the cellulose particles are applied using the above suspension either as such or as a mixture with known binders used in coating pigments such as with starch or a latex, thickening agents e.g. carboxymethyl cellulose, or other additives, in amounts resulting in contents of the cellulose particles in the coating paste typically varying from 80 to 95% by weight. Application on a paper or board web may be accomplished with any known coating process.

The cellulose particles produced by the method of the invention have several advantages in comparison to fillers and coating pigments of the prior art. Critical properties, particularly the strength properties e.g. the bonding strength and tensile index of paper and board may be favourably influenced by the cellulose particles without significant adverse effects on the optical properties. In addition, the grammages of paper and board may be lowered and wear of the machines reduced by using said cellulose particles produced by the method of the invention.

By means of the methods of the invention for producing, and for coating paper and board utilizing the cellulose particles, the proportions of renewable organic materials in papers and boards may be increased, and thus the utilization of papers and boards removed from the recycling system by burning may be improved. Within the European Union, the disposal of compostable materials to landfills will be prohibited in the future, and thus burning will be one of the important alternatives for waste disposal.

EXAMPLES

Example 1

Preparation of Cellulose Particles from Dissolved Cellulose

Bleached softwood pulp was ground in a Valley beater for 1 hour. A sample of 400 g was taken (consistency 13.08 g/l), and the pH was adjusted to a value of 5 using dilute NaOH and HCl solutions. 1 ml of the Pergalase A40 enzyme having an activity of 2316 IU/g and specific weight of 1.11 g/ml was added to the samples thus obtained. The samples were heated in a water bath at 50° C. for 6 hours. Thereafter, a base treatment was performed, said base treatment comprising the addition of 100 g of NaOH dissolved in 70 g of water to the samples, followed by heating of the samples at 45° C. for 6 hours. A solution containing about 0.8% by weight of cellulose was sprayed with a spraying bottle to 1 liter of 1M sulphuric acid in a large beaker. The spraying bottle was equipped with a fan-like nozzle having a spreading angle that may be adjusted in a stepless manner. The spreading angle of the nozzle was here about 60° C., the distance between the nozzle and the sulphuric acid solution being from 20 to 30 cm. Precipitated cellulose particles were recovered from the sulphuric acid solution by filtering and washed. The particles thus prepared from cellulose dissolved by enzyme and base treatments, and useful as fillers and coating pigments in the production of paper and board are shown in FIG. 1.

Example 2

Stiffening of the Structure of Cellulose Particles by Formaldehyde Treatment

Cellulose particles were prepared as described in the preceding example. The particles were, however, not filtered and washed, but remained in the regenerating solution, followed by the adjustment of the $H_2SO_4$ content of the suspension to a value of 0.1 M. 37% formaldehyde containing from 10 to 15% of methanol, 5 moles of formaldehyde per one mole of glucose units was added dropwise to the suspension of the cellulose particles at room temperature, the slurry was heated at 50° C. for 60 minutes and the cellulose particles were recovered by filtering.

Example 3

Use of the Cellulose Particles Treated with Formaldehyde as a Filler in Paper

Sheets were made of pulp consisting of 70% of bleached birch pulp and 30% of bleached softwood pulp, the sheets containing as a filler cellulose particles produced and treated with formaldehyde as described in the preceding examples, having sizes of 1.5 to 8 µm. Sheets without any filler and sheets containing microcrystalline cellulose or precipitated calcium carbonate as the filler served as controls, respectively. Sheets having grammages of 60 g/m² were made according to the standard SCAN-C 26:76. The filler contents were about 6%, and 14%, by weight. The light scattering coefficients, bonding strengths as Scott Bond values, and tensile indices for the sheets were determined with methods according to SCAN-P 8:93, TAPPI T 569, and SCAN-P 67:93.

Figure 2A:
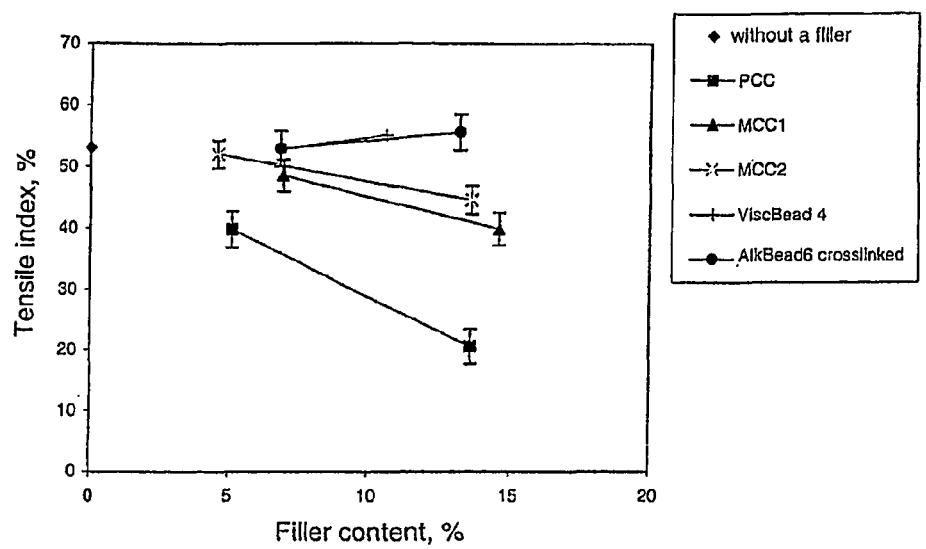
Figure 2B:
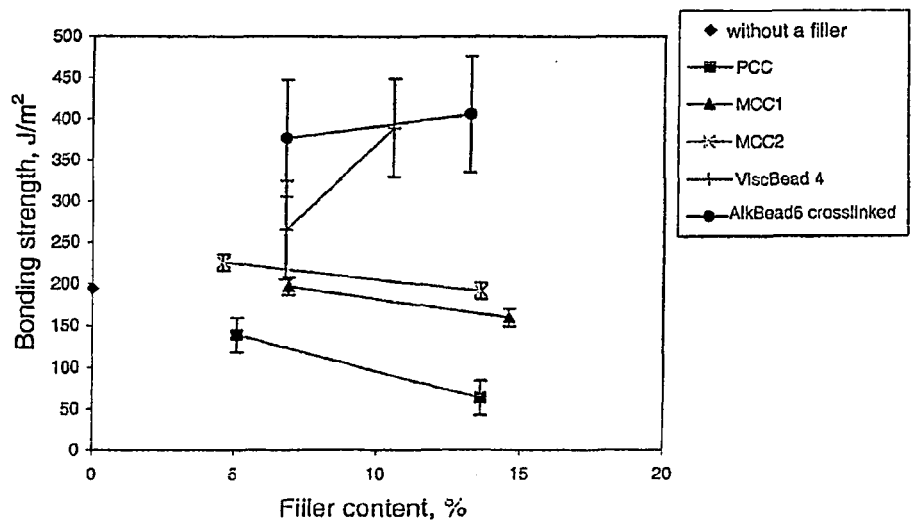
Figure 2C:
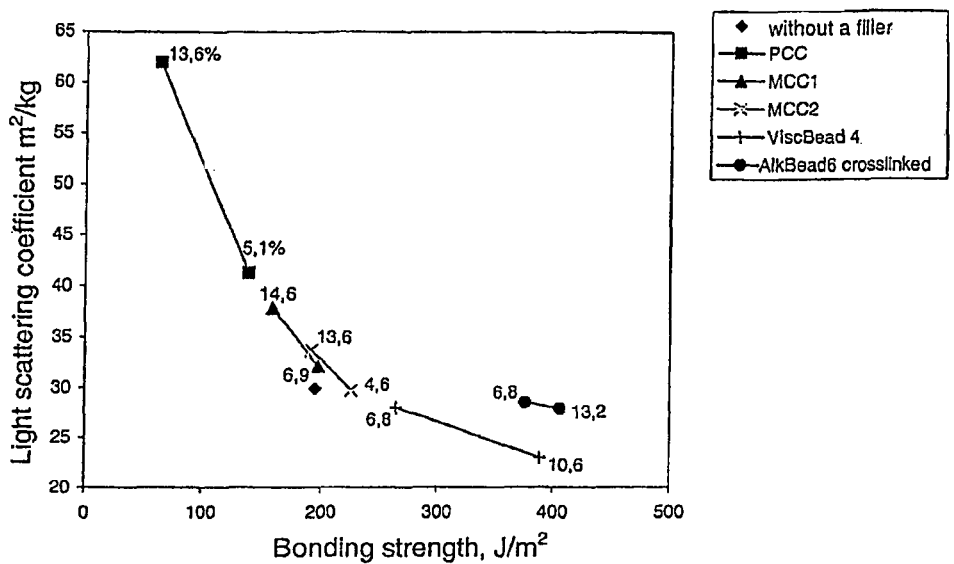
Figure 2D:
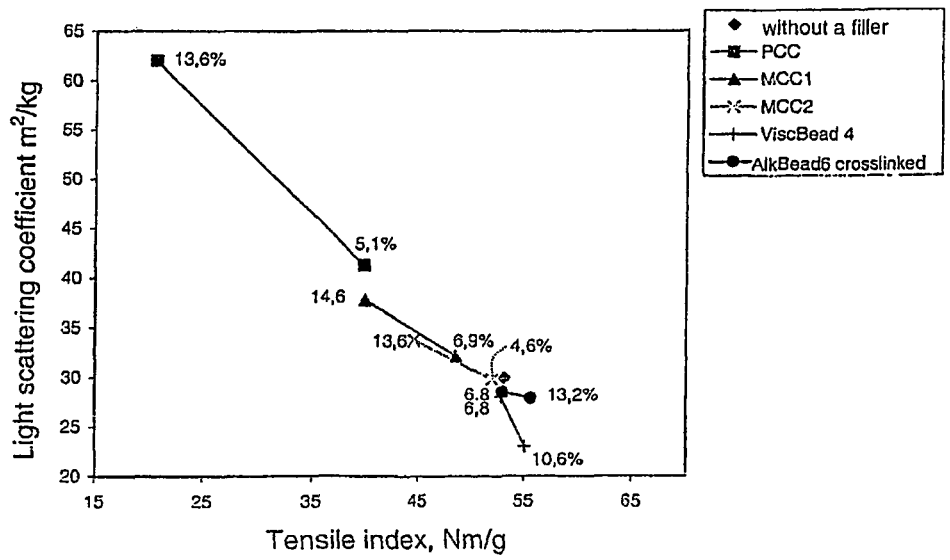

FIGS. 2a, 2b, 2c and 2d, respectively, graphically present the tensile index as a function of filler content, bonding strength as a function of filler content, light scattering coefficient as a function of the bonding strength, and the light scattering coefficient as a function of the tensile index. As may be seen from FIGS. 2a and 2d, strength properties of the sheets may be improved using cellulose particles produced and stiffened by formaldehyde treatment according to the method of the invention, in comparison to precipitated calcium carbonate and microcrystalline cellulose. FIGS. 2c and 2d show that the strength properties of the sheets are improved by using cellulose particles produced and stiffened by formaldehyde treatment according to the method of the invention without hardly any detrimental effects on optical properties.

The invention claimed is:
1. Method for dissolving cellulose, said method consisting of the steps of
   a) preparing an aqueous suspension of cellulose having a cellulose content of at least 0.1% by weight;
   b) adjusting the pH value of the suspension obtained in step a) to a value of from 3 to 7;

c) adding to the suspension an enzyme with endoglucanase activity in an amount wherein the endoglucanase activity is from 20 to 2000×10$^3$ IU/kg of dry pulp to obtain a mixture;

d) heating the mixture obtained in step c) at a temperature between 40 and 65° C. until the degree of polymerization of the cellulose is not lower than a value of 100;

e) adding an alkali or alkaline earth metal hydroxide in an amount above 15% by weight to the mixture obtained in step d); and f) heating the mixture obtained in step e) at a temperature between 15 and 50° C., to obtain a cellulose solution comprising at least 50% dissolved cellulose; and, optionally, g) removing air and solids from the cellulose solution.

2. Method according to claim 1, wherein the cellulose is ground cellulose.

3. Method according to claim 1, wherein the alkali or alkaline earth metal hydroxide is NaOH in an amount ranging from 15.5 to 30%, by weight.

4. Method of obtaining precipitated cellulose particles, said method consisting of the steps of a) preparing an aqueous suspension of cellulose having a cellulose content of at least 0.1% by weight;

b) adjusting the pH value of the suspension obtained in step a) to a value of from 3 to 7;

c) adding to the suspension an enzyme with endoglucanase activity in an amount wherein the endoglucanase activity is from 20 to 2000×10$^3$ IU/kg of dry pulp to obtain a mixture;

d) heating the mixture obtained in step c) at a temperature between 40 and 65° C. until the degree of polymerization of the cellulose is not lower than a value of 100;

e) adding an alkali or alkaline earth metal hydroxide in an amount above 15% by weight to the mixture obtained in step d);

f) heating the mixture obtained in step e) at a temperature between 15 and 50° C., to obtain a cellulose solution comprising at least 50% dissolved cellulose; and g) spraying or mixing the cellulose solution obtained in step f) into an acid solution to obtain a suspension containing precipitated cellulose particles, and, optionally, subjecting the precipitated cellulose particles in the suspension to crosslinking or derivatization; and, optionally, h) washing and/or drying the precipitated cellulose particles of step g).

5. Method according to claim 4, wherein cellulose content of the cellulose solution obtained in step g), and droplet size in case of spraying, or mixing speed in case of mixing are selected such that the obtained precipitated cellulose particles have particle sizes ranging between 0.05 and 10 μm.

6. Method according to claim 4, wherein the crosslinking is achieved by adding 5 moles of formaldehyde per one mole of glucose units to the suspension containing precipitated cellulose particles and heating the resulting suspension at 40 to 60° C. to obtain precipitated crosslinked cellulose particles.

* * * * *